United States Patent [19]

Uehara et al.

[11] Patent Number: 5,556,622

[45] Date of Patent: Sep. 17, 1996

[54] METHOD OF TREATMENT FOR STOMA-PERIPHERAL INFLAMMATION DISEASES

[75] Inventors: Yasuo Uehara, Iruma; Michihito Ise, Kawagoe, both of Japan

[73] Assignee: Kureha Kagaku Kogyo Kabushiki Kaisha, Japan

[21] Appl. No.: 450,466

[22] Filed: May 25, 1995

[30] Foreign Application Priority Data

May 27, 1994 [JP] Japan .................................. 6-138071

[51] Int. Cl.⁶ .................................................. A61K 33/44
[52] U.S. Cl. .................................................. 424/125
[58] Field of Search .................................................. 424/125

[56] References Cited

U.S. PATENT DOCUMENTS

| | | | |
|---|---|---|---|
| Re. 29,101 | 1/1977 | Amagi et al. | 423/449 |
| 3,917,806 | 11/1975 | Amagi et al. | 423/449 |
| 4,420,443 | 12/1983 | Kaji et al. | 264/15 |
| 4,681,764 | 7/1987 | Endo et al. | 424/125 |
| 4,761,284 | 8/1988 | Nishimura | 424/125 |

FOREIGN PATENT DOCUMENTS 61-1366  8/1986  Japan.

*Primary Examiner*—Marianne M. Cintins
*Assistant Examiner*—William R. A. Jarvis
*Attorney, Agent, or Firm*—Nixon & Vanderhye

[57] ABSTRACT

The disclosure describes a method of treating a patient suffering from stoma-peripheral inflammation diseases, comprising orally administering to said patient an effective amount of a pharmaceutical composition in dosage unit form comprising a spherical activated carbon having a particle size of 0.05 to 2 mm.

3 Claims, No Drawings

METHOD OF TREATMENT FOR STOMA-PERIPHERAL INFLAMMATION DISEASES

BACKGROUND OF THE INVENTION

The present invention relates to a method of treatment for stoma (enteroproctia)-peripheral inflammation diseases, and more particularly, to a treatment for stoma (enteroproctia)-peripheral inflammation diseases by administering to the patient a pharmaceutical composition for stoma (enteroproctia)-peripheral inflammation diseases, which comprises an activated carbon as an active ingredient.

The stoma (enteroproctia)-peripheral inflammation diseases is a trouble incidental to an enteroproctia (stoma) installed after resection of an intestinal part affected by a disease such as ulcerative colitis, Crohn's disease or hemorrhoidal disease. Namely, the stoma (enteroproctia)-peripheral inflammation diseases is inflammation of the skin around the enteroproctia (stoma) installed after resection of the affected part of the bowel. Since the enteroproctia (stoma) has no sphincteral muscle, the patient can not evacuate the bowels by relaxing the sphincteral muscle as a person with the normal anus, the evacuation is made regardless of the patient's will. Therefore, various inflammatory troubles such as rash, itching, redness, erosion, etc., tend to produce in the skin around the enteroproctia (stoma), principally due to frequent evacuation, defiling by leakage or scatter of excreta and attachment of the collecting bag to the patient's skin.

The enteroproctia (stoma) is mostly installed to the cases of rectal cancer, anal cancer, rectal ulcer, rectal polyp, infiltration of cystic cancer or uterine cancer to the rectum, spinal cord injury, ulcerative coliris, Crohn's disease, familial polyposis, rectal inflammation, ileus, anal atresia, megacolon and other like diseases.

The patient who has installed the enteroproctia (stoma) gets into distress when constipated since he can not control evacuation of his own will. Also, as the collecting bag touches the skin, the attached part of the skin is stimulated to form an eruption (rash). Further, due to frequent evacuation and defiling by leakage or scatter of excreta, there frequently produces inflammation of the skin around the enteroproctia (stoma) to give a great deal of discomfort to the patient.

Skin protective agents, emulsions, creams, antiphlogistics, antibiotics, etc., are used for the treatment of stoma (enteroproctia)-peripheral inflammation diseases, but it is impossible to perfectly cure of inflammation by such medication.

Thus, the development of a pharmaceutical composition capable of producing a definite therapeutic effect for stoma (enteroproctia)-peripheral inflammation diseases without causing side effects such as constipation has been demanded.

As a result of the present inventors' studies on an effective therapeutic agent for stoma (enteroproctia)-peripheral inflammation diseases, which is different from the conventional medicines, it has been found that the prominent therapeutic effect for the stoma (enteroproctia)-peripheral inflammation diseases by oral administration of a spherical activated carbon. Spherical activated carbons have been conventionally used as an oral therapeutic agent for chronic renal failure, but no report has ever been made on use of such spherical activated carbon as a therapeutic agent for the stoma (enteroproctia)-peripheral inflammation diseases. In view of this circumstance, the above finding by the present inventors is deemed an unexpected fact based on a novel conception. The present invention has been attained on the basis of the above finding.

SUMMARY OF THE INVENTION

An object of the present invention is to provide a pharmaceutical composition and a method for treating stoma (enteroproctia)-peripheral inflammation diseases, which show an excellent therapeutic effect, without causing any specific side effects, for the stoma (enteroproctia)-peripheral inflammation diseases which had hitherto no effective cure.

To attain the above aim, in a first aspect of the invention, there is provided a method of treating a patient suffering from a stoma (enteroproctia)-peripheral inflammation diseases, comprising orally administering to the patient an effective amount of a pharmaceutical composition in dosage unit form comprising a spherical activated carbon having a particle size of 0.05 to 2 mm.

In a second aspect of the invention, there is provided a method of treating a patient suffering from a stoma (enteroproctia)-peripheral inflammation diseases, comprising orally administering to the patient an effective amount of a pharmaceutical composition in dosage unit form comprising a spherical activated carbon having a particle size of 0.05 to 2 mm and produced by heat-treating a porous and spherical carbonaceous substance obtainable from a petroleum-based heavy hydrocarbon (petroleum pitch) in an oxidative atmosphere and further heat-treating the thus obtained substance in an atmosphere inert to carbon.

In a third aspect of the invention, there is provided a method of treating a patient suffering from a stoma (enteroproctia)-peripheral inflammation diseases, comprising orally administering to the patient an effective amount of a pharmaceutical composition in dosage unit form comprising a spherical activated carbon having a particle size of 0.05 to 2 mm, a specific surface area of 500 to 2,000 $m^2/g$ and a specific pore volume of 0.2 to 2.0 ml/g determined in the range of a pore radius of not more than 80 Å.

DETAILED DESCRIPTION OF THE INVENTION

The activated carbon used as an active ingredient of the therapeutic agent for stoma (enteroproctia)-peripheral inflammation diseases according to the present invention is a spherical activated carbon having a particle size of 0.05 to 2 mm, preferably 0.1 to 1.0 mm, which is usable internally for medicinal application. When the particle size of the spherical activated carbon is less than 0.05 mm, harmful side effects such as constipation, etc. may be caused on administration of such spherical activated carbon, and when its particle size exceeds 2 mm, such spherical activated carbon is not only hard to be taken by patient but also slow to take effect.

It is preferable that the spherical activated carbon used in the present invention has high adsorptivity. For this purpose, the spherical activated carbon is preferably one which has a specific surface area of 500 to 2,000 $m^2/g$. The specific surface area has been determined according to the methanol adsorption method using an automatic adsorption meter.

For producing the spherical activated carbon used in the present invention, there can be used suitable raw materials which are easily available, such as sawdust, coal, coconut shell flour, petroleum or coal pitches, or organosynthetic high polymeric substances. The spherical activated carbon is produced by a process of carbonizing the raw material and activating the obtained carbon. Various processes for activation such as a steam activation process, chemicals activation process, an air activation process, a carbon dioxide activation, etc., can be used.

Examples of the spherical activated carbons available for use in the present invention are a granulated spherical activated carbon produced from carbonaceous powders, a spherical activated carbon produced by calcining a resin, and a spherical activated carbon obtainable from petroleum-based heavy hydrocarbons (petroleum pitches). The spherical activated carbon has the advantages over the powdery activated carbon in that the spherical activated carbon does not scatter when administered and also won't cause constipation even if administered continuously, and thus is suited as an active ingredient of the pharmaceutical composition according to the present invention.

Among the spherical activated carbons, those obtainable from petroleum-based heavy hydrocarbons (petroleum pitches), which are homogeneous spherical particles, are preferred.

The granulated activated carbon produced from carbonaceous powders can be obtained by granulating the carbonaceous powder material into microspherical particles with a binder such as tar or pitch, heat-treating the obtained particles at 600° to 1,000° C. in an inert atmospheres for carbonization, and activating the produced carbon particles. Various processes can be used for activation of the carbon particles, such as the steam activation process, the chemicals activation process, the air activation process and the carbon dioxide activation process. The steam activation process, for instance, is carried out at 800° to 1,100° C. in a steam atmosphere.

The spherical activated carbon produced by calcining a resin is produced, for instance, in the manner described in Japanese Patent Application Publication (KOKOKU) No. 61-1366. For example, a condensation or polyaddition-type thermosetting prepolymer is mixed with a curing agent, curing catalyst, emulsifier, etc., and the obtained mixture is emulsified in water with stirring and reacted while continuing the stirring at room temperature or under heating. The reaction system first assumes a state of a suspension, and on further stirring, produces a spherical product of thermosetting resin. This product is recovered and heated at a temperature of not less than 500° C. in an inert atmosphere to carbonize the spherical product, and the obtained spherical carbon product is activated by the method mentioned above.

The spherical activated carbon obtainable from petroleum pitches can be produced, for instance, by the processes such as described below.

In a first process, as for instance described in Japanese Patent Publication (KOKOKU) No. 51-76 (corresponding to U.S. Pat. No. 3,917,806) and Japanese Patent Application Laid Open (KOKAI) No. 54-89010 (corresponding to U.S. Pat. No. 4,761,284), a petroleum pitch having a flow point of 50° to 300° C. is made into spherical particles in a molten state, then infusibilized with oxygen, carbonized at a temperature of 600° to 1,000° C. in an inert atmosphere and activated at a temperature of 850° to 1,000° C. in a steam atmosphere. Carbonization and activation can be accomplished simultaneously by selecting a proper atmosphere.

According to a second method, as for instance described in Japanese Patent Publication (KOKOKU) No. 59-10930 (corresponding to U.S. Pat. No. 4,420,443), a petroleum pitch having a flow point of not less than 160° C. is made into strings, crushed, put into hot water to form spherical particles, infusibilized with oxygen, and then carbonized and activated in the same way as the first process described above.

The spherical activated carbon particles obtained according to the above-described first or second process have a particle diameter of 0.05 to 2.0 mm, preferably 0.1 to 1.0 mm; a specific surface area of 500 to 2,000 m$^2$/g, preferably 1,000 to 2,000 m$^2$/g.

Further, as the activated carbon as an active ingredient of the pharmaceutical composition according to the present invention, a spherical activated carbon obtainable by subjecting to an oxidation and reduction treatments may be usable.

The spherical activated carbon material as a raw material for subjecting to the oxidation and reduction treatments may be either of a porous and spherical carbonaceous substance obtainable from petroleum pitch, a granulated carbon obtainable from carbonaceous powders, or a spherical carbon obtainable by calcining a resin, but the porous and spherical carbonaceous substance obtainable from petroleum pitches is preferred.

As the process of the oxidation and reduction treatments at high temperature, a process described in Japanese Patent Publication (KOKOKU) No. 62-11611 (corresponding to U.S. Pat. No. 4,681,764) may be exemplified.

The oxidation treatment at a high temperature is a heat-treatment carried out in an oxidative atmosphere containing oxygen at a high temperature, for example, 300° to 700° C. As the oxygen source, there may be used pure oxygen, nitrogen oxide and air. The reduction treatment at a high temperature is a heat-treatment carried out at a high temperature, for example, 700° to 1,100° C. in an atmosphere inert to carbon. The atmosphere inert to carbon can be formed by using nitrogen gas, argon gas, helium gas or a mixture thereof.

The oxidation treatment is preferably carried out in an atmosphere with an oxygen content of 0.5 to 25% by volume, more preferably 3 to 10% by volume at a temperature of 300°0 to 700° C., more preferably 400° to 600° C. The reduction treatment is preferably carried out in an inert atmosphere at a temperature of 700° to 1,100° C., more preferably 800° to 1,000° C.

In the production of the spherical activated carbon obtainable from the porous and spherical carbonaceous substance obtainable from petroleum pitches, it is preferred that the oxidation treatment is carried out at a temperature of 350° to 700° C. in an oxidative atmosphere and then the heat-treatment is carried out at a temperature of 800° to 1,000° C. in an atmosphere inert to carbon.

More in detail, the process for producing the spherical activated carbon obtainable from the porous and spherical carbonaceous substance obtainable from petroleum pitches, which comprises the steps of:

(1) blending a petroleum-based heavy hydrocarbon (petroleum pitch) of a H/C ratio of 0.45 to 0.80 and a flow point of 100° to 300° C., in which the presence of unevenly distributed anisotropic regions is not observed under a polarization microscope, with an aromatic hydrocarbon such as benzene and naphthalene;

(2) dispersing the obtained mixture in hot water at 100° to 180° C. containing a surfactant while stirring the resultant dispersion, to form particles thereof;

(3) after cooling the resultant dispersion to room temperature, separating the thus formed particles by filtration;

(4) removing the aromatic hydrocarbon contained in the particles by extraction with an organic solvent such as hexane and methanol;

(5) contacting the thus extract-treated particles with a flow of oxidative gas to carry out the oxidation of the particles (infusibilization);

(6) heating the thus infusibilized particles in a flow of a gas which is reactive with carbon, such as steam and carbon dioxide, at a temperature of 800° to 1,000° C. (carbonization and activation);

(7) heat-treating the thus obtained porous and spherical carbonaceous substance at a temperature of 350° to 700° C. in an atmosphere containing 0.5 to 20% by volume of oxygen; and (8) further heat-treating the thus obtained substance at a temperature of 800° to 1,000° C in an atmosphere inert to carbon.

Such spherical activated carbon subjected to the oxidation and reduction treatments have a particle diameter of 0.05 to 2.0 mm, preferably 0.1 to 1.0 mm; a specific surface area of 500° to 2,000 $m^2/g$, preferably 1,000 to 2,000 $m^2/g$; and a specific pore volume of 0.2 to 2.0 ml/g determined in the range of pore-radius of less than 80 Å.

As an example of the spherical activated carbon obtained by subjecting the porous and spherical carbonaceous substance derived from the petroleum pitches to the oxidation and reduction treatments, KREMEZIN (produced by Kureha Chemical Industries Co., Ltd.) used as an oral therapeutic agent for a chronic renal failure, can be cited.

KREMEZIN is a spherical activated carbon produced by the process disclosed in Japanese Patent Publication (KOKOKU) No. 62-11611 (corresponding to U.S. Pat. No. 4,681,764), which has a particle size of about 0.2 to 0.4 mm and is a homogeneous spherical particle (which is not spherical particle produced by granulating a carbon powder).

When KREMEZIN which is a commercially available spherical activated carbon used as an oral therapeutic agent for a chronic renal failure, and is one of the spherical activated carbons usable in the present invention, is orally administered to the patients suffering from stoma (enteroproctia)-peripheral inflammation diseases, there is observed quite surprisingly a definite therapeutic effect of the spherical activated carbon, leading to a remarkable betterment of the disease. Further, no side effect such as constipation is caused after administration of the spherical activated carbon. In view of these facts, it is recognized that the pharmaceutical composition of the present invention comprising the spherical activated carbon as an active ingredient is useful as a therapeutic agent for the stoma (enteroproctia)-peripheral inflammation diseases.

From the result of an acute toxicity test, it is determined that $LD_{50}$ of the spherical activated carbon according to the present invention is not less than 5,000 mg/kg. Also, in an anatomical examination conducted two weeks after and in the observation of external appearance and the viscera, there is seen no noteworthy abnormality nor any notable toxic symptoms. Further, in a subacute toxicity test, there is observed no notable abnormality nor toxic symptoms attributable to administration of the specimen. These facts attest to very high safety of the spherical activated carbon according to the present invention.

The pharmaceutical composition for stoma (enteroproctia)-peripheral inflammation diseases according to the present invention can be applied to man and mammals. It is preferably administered orally. The dosage of the pharmaceutical composition depends on the subject of administration (man or animal), age thereof, individual difference, condition of the disease and other factors. For human, the dosage of the pharmaceutical composition (calculated as the amount of the spherical activated carbon) is usually 0.2 to 20 g, preferably 1 to 10 g per day. The dosage may be properly increased or decreased according to the condition of the disease. Also, a day's dose of the pharmaceutical composition according to the present invention may be administered all at once or in portions.

Spherical activated carbon may be administered in the form as it is or in the form of a pharmaceutical preparation. In the former case, activated carbon may be suspended in drinking water to form a slurry which is convenient to take.

The pharmaceutical preparations comprising activated carbon may take a diversity of forms such as granule, tablet, sugar-coated tablet, capsule, stick, divided package, suspension, etc. In the case of capsule, it may not necessarily be ordinarily used gelatin capsule, enteric-diffluent capsule may be used as occasion demand. In case the composition is used in the form of granules, tablet or sugar-coated tablet, such granules or tablets need to be released into the original form of spherical activated carbon particles in the viscera. The content of spherical activated carbon in the pharmaceutical compositions is usually 1 to 100 wt %. In the present invention, the preferred forms of pharmaceutical preparation comprising spherical activated carbon are capsule, stick and divided package. In these preparations, spherical activated carbon is encapsulated or packed in a container in the form as it is.

Capsules can be obtained by, for example, encapsulating 200 mg of spherical activated carbon in a gelatin capsule.

Sticks can be prepared by, for example, packing 2 g of spherical activated carbon in a stick composed of a laminate film and heat-sealing the packed stick.

The pharmaceutical composition of the present invention, which is administered orally, shows a definite therapeutic effect for the stoma (enteroproctia)-peripheral inflammation diseases.

EXAMPLES

The present invention is explained in more detail in the following Examples, however, it should be recognized that the scope of the invention is not restricted to these Examples.

Production Example (Preparation of spherical activated carbon)

Three hundred grams of a petroleum-based heavy hydrocarbon (petroleum pitch) having an H/C ratio of 0.55 and a flow point of 220° C. and not having localized presence of an isotropic region in observation under a polarization microscope, and 100 g of naphthalene were introduced into an autoclave provided with a stirrer, and the obtained mixture was further mixed well at a temperature of 180° C. Into the thus obtained liquid mixture was added 1,200 g of an aqueous 0.5% solution of polyvinyl alcohol. Then the resultant mixture was vigorously stirred at a temperature of 140° C. for 30 minutes and cooled to room temperature with stirring to form a dispersion of spherical particles. After separating the spherical particles therefrom, the obtained spherical particles were treated with hexane in an extractor to remove naphthalene contained in the particles and dried by air flow. The thus obtained spherical particles were heated to 300° C. at a rate of 25° C./hr by a flow of heated air in a fluidized bed and further kept for 2 hours at the same temperature. The obtained spherical particles were heated to 900° C. by steam in a fluidized bed and further kept for 2 hours at the same temperature to obtain spherical carbonaceous particles.

The obtained spherical carbonaceous particles were heated to 610° C. in an atmosphere containing 3% by volume of oxygen and further kept at the same temperature for 3 hours in the same atmosphere. Then the treated spherical carbonaceous particles were further heated to 940° C. in an atmosphere of nitrogen and then kept at the same temperature for 30 minutes in the same atmosphere to obtain spherical activated carbon (spherical particulate activated carbon having a particle size of about 0.2 to about 0.4 mm, obtained by subjecting spherical and porous particulate carbonaceous substance produced from a petroleum-based heavy hydrocarbon (petroleum pitch) to the oxidation and reduction treatments at a high temperature).

The obtained spherical activated carbon was homogeneous and substantially truly spherical particles, and had a particle diameter of about 0.2 to about 0.4 mm, a specific surface area of 1520 $m^2/g$, and a specific pore volume of 0.72 ml/g determined in the range of a pore-radius of not more than 80 Å.

Test Example (Toxicity test on spherical activated carbon obtained in the Production Example)

In an acute toxicity test of the spherical activated carbon by oral administration to the rats (Cpb:WU; Wister-Random), no abnormality was observed even at the maximum dosage (5,000 mg/kg for male and female rats) according to the Guidelines for Toxicity Studies of Drugs (Notification No. 118 of the Pharmaceutical Affairs Bureau, Ministry of Health and Welfare, Japanese Government, Feb. 15, 1984).

Example 1

(Effect on inflammation of skin around ileac stoma)

The subject was a man (26 years old) suffering from Crohn's disease. He had installed a ileac stoma because of stricture at the termination of the ileum and partial abdominal abscess four years ago. Redness and ulceration of the skin around the ileac stoma occurred frequently. Various treatments were applied for eliminating these troubles, but in vain. When the capsules containing 200 mg of the spherical activated carbon obtained in the Production Example were administered to the patient at a ratio of 30 capsules per day, there were noted the signs of improvement of the condition of the disease, such as the cutaneous lesion around the ileac stoma at the 4th day after start of administration of the spherical activated carbon, and it perfectly disappeared on the 7th day after start of administration thereof.

Example 2

(Effect on cutaneous inflammation around ileac stoma or colonic stoma)

The subjects were three men installed each ileac stoma due to ileus, and two men and one woman installed each colonic stoma due to rectal stenosis. Circumspection was used for the care of the stoma, but the hypersensitivity of the skin was not improved. Inflammatory troubles such as erosion, redness, etc., occurred in the skin around the stoma in each case.

When the capsules containing 200 mg of the spherical activated carbon obtained in the Production Example were administered to the patients at a ratio of 30 capsules per day, the skin erosion, redness and other subjective symptoms around the stoma were improved without constipation caused. Even when the pack (pouch) was imperfectly applied to the stoma, the skin troubles have vanished in 2 to 3 days, a period in which the pack (pouch) is replaced with new one, and it also became possible to set the pack in place smoothly. Thereafter, each patient showed a favorable progress. It was thus found that the spherical activated carbon is very useful for the treatment of cutaneous lesion around stoma which tends to produce after installing the stoma.

What is claimed is:

1. A method of treating stomaperipheral inflammation diseases in a patient in need thereof, comprising orally administering to said patient an effective amount of a pharmaceutical composition in dosage unit form comprising a spherical activated carbon having a particle size of 0.05 to 2 mm.

2. A method according to claim 1, wherein said spherical activated carbon is produced by heat-treating a porous and spherical carbonaceous substance obtainable from a petroleum-based heavy hydrocarbon in an oxidative atmosphere and further heat-treating the thus obtained substance in an atmosphere inert to carbon.

3. A method according to claim 1, wherein said spherical activated carbon has a specific surface area of 500 to 2,000 $m^2/g$ and a specific pore volume of 0.2 to 2.0 ml/g as determined in the range of a pore radius of not more than 80 Å.

\* \* \* \* \*